United States Patent [19]

Bilstad et al.

[11] 4,305,659

[45] Dec. 15, 1981

[54] PHOTOMETRIC APPARATUS AND METHOD

[75] Inventors: Arnold C. Bilstad, Deerfield; Richard I. Brown, Northbrook; Michael Wicnienski, Antioch, all of Ill.

[73] Assignee: Baxter Travenol Laboratories, Inc., Deerfield, Ill.

[21] Appl. No.: 127,732

[22] Filed: Mar. 6, 1980

[51] Int. Cl.³ .................... G01N 33/48; G01N 21/21
[52] U.S. Cl. .................................... 356/40; 356/435
[58] Field of Search ............. 356/40, 41, 321, 322, 356/408, 433–435, 409, 420

[56] References Cited

U.S. PATENT DOCUMENTS

| | | | |
|---|---|---|---|
| 1,894,132 | 1/1933 | Stone | 356/322 |
| 2,358,992 | 9/1944 | Millikan . | |
| 2,640,389 | 6/1953 | Liston . | |
| 2,803,752 | 8/1957 | Warren | 356/435 X |
| 3,332,313 | 7/1967 | Batson | 356/434 X |
| 3,522,739 | 8/1970 | Coor et al. . | |
| 3,647,299 | 3/1972 | Lavallee | 356/41 |
| 3,684,378 | 8/1972 | Lord . | |
| 3,720,813 | 3/1973 | Badessa . | |
| 3,730,627 | 5/1973 | Kent . | |
| 3,787,124 | 1/1974 | Lowy et al. . | |
| 3,799,672 | 3/1974 | Vurek | 356/41 |
| 3,804,535 | 4/1974 | Rodriguez | 356/41 X |
| 3,952,206 | 4/1976 | Liedholz | 356/40 X |
| 3,972,614 | 8/1976 | Johansen et al. | 356/40 X |
| 4,136,818 | 1/1979 | Larrabee | 233/1 R |

Primary Examiner—F. L. Evans
Attorney, Agent, or Firm—Paul Flattery; Daniel D. Ryan; George Gerstman

[57] ABSTRACT

Photometric apparatus and method for determining the absorbance ratio, in a sample, of two different wavelength lights. A first light is given a reference intensity and is passed through the sample. A second light is passed through the sample and its intensity is varied so that the intensity of the second light that has passed through the sample is equal to the intensity of the first light that has passed through the sample. When these intensities are equal, the intensity of the second light is detected in a state wherein it has not passed through the sample, resulting in an equivalent to the ratio of the absorbance in the sample of the second light and the first light.

17 Claims, 3 Drawing Figures

TIMING PULSE

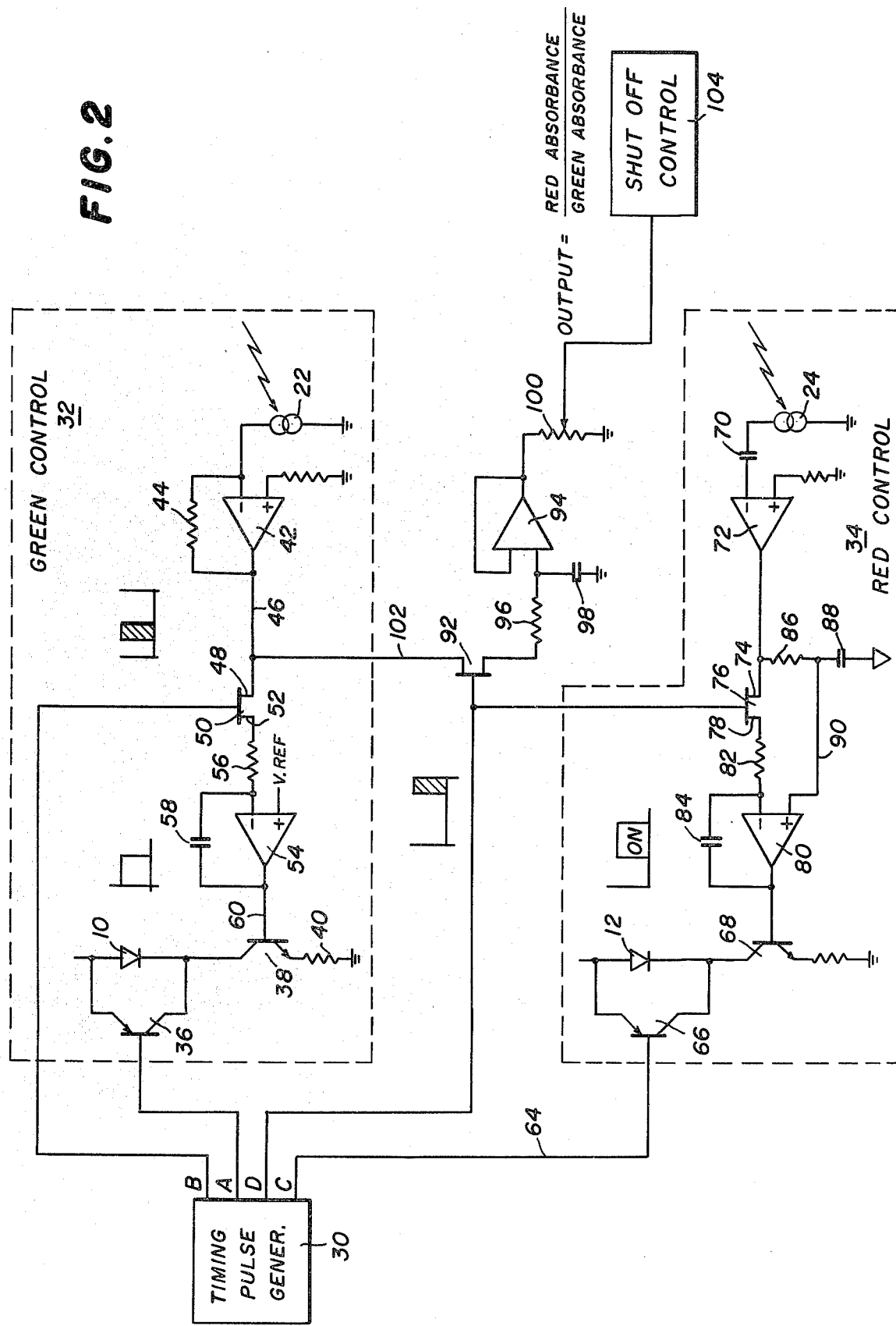

PHOTOMETRIC APPARATUS AND METHOD

BACKGROUND OF THE INVENTION

The present invention concerns a novel photometer and method for determining the absorbance ratio, in a sample, of two lights of different wavelengths. The illustrative embodiment of the invention is directed to a spectrophotometer for determining the presence of hemoglobin in a fluid.

In various applications it is necessary to detect low levels of the various hema complexes, and most particularly oxyhemoglobin and free hemoglobin in a certain fluid. For example, in systems in which plasma is collected, it is often desirable to detect the presence of low levels of hemoglobin in the collected plasma.

In one prior art type of system for detecting hemoglobin in a fluid, the loss of light traveling through the sample is detected. To this end, the operator starts the fluid flow and the output is initially set to zero. Any change in this zero output level is detected and is considered a measure of the increased level of hemolysis. One problem in connection with this prior art device is the fact that a change in turbidity might be detected as an increased level of hemolysis. Another problem is that this prior art system requires an initial zeroing procedure which must be handled properly by an operator. A further problem with respect to this prior art system is that it is subject to changes in ambient light levels.

We have discovered that a hemolysis detector can be provided by determining the red/green absorbance ratio of the sample. In this manner, the presence of even small traces of hemoglobin can be detected in a fluid, such as plasma.

It is, therefore, an object of the present invention to provide an apparatus and method for determining the absorbance, in a sample, of two different wavelength lights.

Another object of the present invention is to provide a hemolysis detector which operates to detect hemoglobin in a fluid by determining the red/green absorbance ratio of the fluid.

Another object of the present invention is to provide a system for determining the color of a sample by using known absorbance characteristics and passing two colors through the sample and then determining the ratio of absorbance of the two colors.

A still further object of the present invention is to provide apparatus and a method for determining the color absorbance ratio of a fluid, with the apparatus and method being relatively blind to changes in turbidity.

A further object of the invention is to provide an apparatus and method for determining the color absorbance ratio of a fluid with the apparatus and method being blind to ambient light level changes.

A further object of the present invention is to provide an apparatus for determining the color absorbance ratio of a sample, with the apparatus being relatively simple in construction and easy to manufacture.

Other objects and advantages of the invention will become apparent as the description proceeds.

SUMMARY OF THE INVENTION

In accordance with the present invention, a photometric apparatus and method are provided for determining the absorbance ratio in a sample, of two lights having different wavelengths. The first light has a reference intensity or its intensity is varied so that it is equal to a reference standard. The first light and the second light are passed through the sample and their respective intensities after they have passed through the sample are detected. The intensity of the second light that has passed through the sample is varied so that it is equal to the intensity of the first light that has passed through the sample. When the intensities of the lights that have passed through the sample are equal, the intensity of the second light is detected in a state wherein it has not passed through the sample. This last-mentioned intensity is equivalent to the ratio of the absorbance of the second light and the first light.

In the illustrative embodiment, the red/green absorbance ratio of plasma is detected in order to determine the presence of hemoglobin. A green light is provided and a red light is provided. The intensity of the green light is detected and is varied so that it is equal to a reference standard. The green light and the red light are passed through the plasma and the respective intensities of the green light and the red light are detected after they have passed through the plasma. The intensity of the red light that has passed through the sample is varied so that it is equal to the intensity of the green light that has passed through the sample. Once the intensity of the red light that has passed through the sample is equal to the intensity of the green light that has passed through the sample, the intensity of the red light is then detected in a state wherein it has not passed through the sample. The intensity of the red light that has not passed through the sample is equivalent to the ratio of the absorbance of the red light and the green light.

In the illustrative embodiment, the intensities of the green light and the red light passed through the plasma are averaged and this average forms a reference for the control of the intensity of the red light passing through the sample.

A more detailed explanation of the invention is provided in the following description and claims, and is illustrated in the accompanying drawings.

BRIEF DESCRIPTION OF THE DRAWINGS

FIG. 2 is a schematic circuit diagram of a control circuit for the photometer of FIG. 1.

DETAILED DESCRIPTION OF THE ILLUSTRATIVE EMBODIMENT

Figure 1:
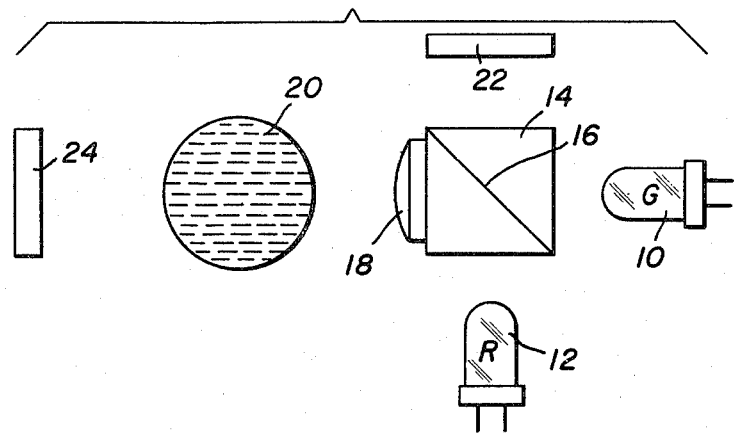
FIG. 1 is a diagram of a photometer constructed in accordance with the principles of the present invention.

Referring to FIG. 1, a photometer apparatus is shown therein comprising a first source of light 10 having a first wavelength, a second source of light 12 having a second wavelength, a cube beam splitter 14 having a mirror 16 which preferably reflects 50 percent of the light impinging upon it and transmits 50 percent of the light through the mirror, a collimating lens 18 for detecting light from the beam splitter 14 through sample 20, a first photodetector 22 and a second photodetector 24. It should be understood that the reflection-transmission ratio of mirror 16 may be other than 50:50.

In the illustrative embodiment, the photometer system is used to detect hemoglobin in plasma that is being collected. Thus sample 20 comprises the plasma and it has been found satisfactory to provide light source 10 in the form of a green light emitting diode (LED) having a peak wavelength of 565 nm, and light source 12 in the form of a red LED having a peak wavelength of 635 nm.

Green light 10 and red light 12 are perpendicularly located with respect to each other and with respect to beam splitter 14. Photodetector 22 is positioned opposite beam splitter 14 from red light 12 and photodetector 24 is positioned opposite beam splitter 14 from green light 10, with the sample 20 interposed between photodetector 24 and beam splitter 14. Collimating lens 18 operates to direct the light from beam splitter 14 through the sample and to photodetector 24.

Since beam splitter 14 operates to reflect half the light and transmit half the light, both the red and green lights will impinge on both detectors, with photodetector 22 receiving unabsorbed radiation and photodetector 24 receiving the absorbed radiation after passing through sample 20.

In order to determine the red/green absorbance ratio of the plasma 20, the intensity of the green light from LED 10 is detected by photodetector 24 and the intensity of LED 10 is varied so that the intensity is equal to a predetermined reference standard. The reference green light from LED 10 and the red light from LED 12 are directed through plasma 20 and the respective intensities of the red and green lights after they have passed through the plasma 20 are detected by photodetector 24. The intensity of LED 12 is then varied so that, as detected as photodetector 24, it is equal to the intensity of LED 10 as detected by photodetector 24. When photodetector 24 detects that both intensities of the green light from LED 10 and the red light from LED 12 are equal, the then prevailing intensity of the red light from LED 12 is detected by photodetector 22, which effectively detects the intensity of the red light in a state wherein it has not passed through plasma 20. The intensity of the red light as detected by photodetector 22 is then equivalent to the ratio of the absorbance of the red light and the green light.

Figure 3:
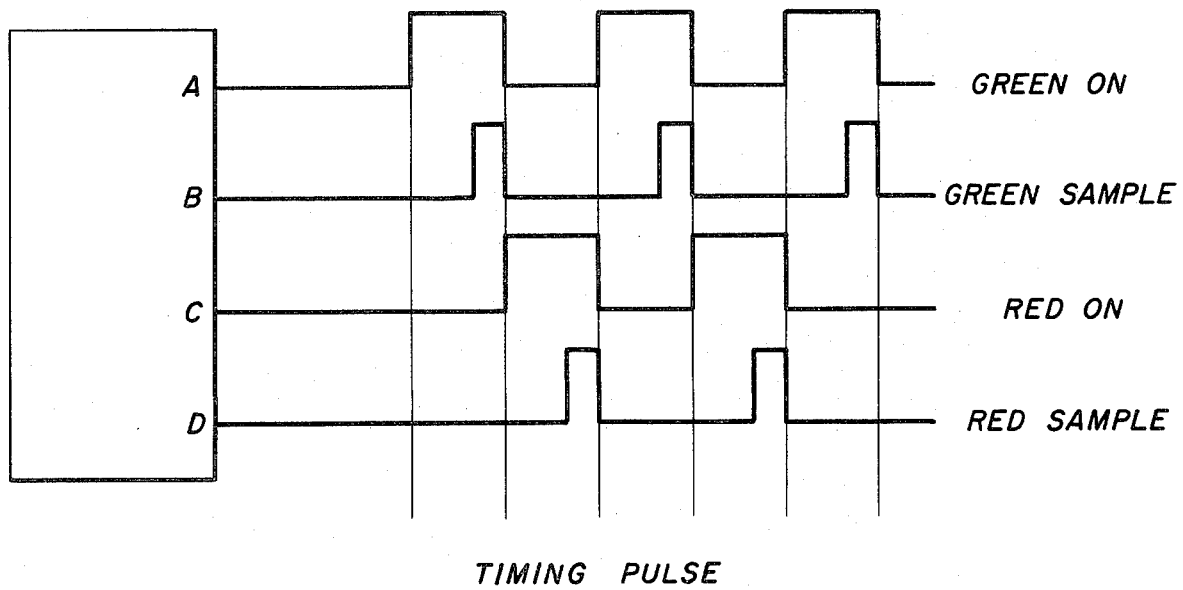
FIG. 3 is a timing diagram showing, in time reference, the timing pulses provided by the timing pulse generator of the control circuit of FIG. 2.

The control circuit for achieving the above objectives is illustrated in FIG. 2 with the timing diagram being illustrated in FIG. 3. Referring now to FIG. 2, a timing guide pulse generator 30 is shown therein having four outputs A, B, C and D. As illustrated in FIG. 3, output A is the "green on" signal and output B is the "green sample" signal. It can be seen that the "green sample" signal is the trailing portion of the "green on" signal.

Signal C from the timing pulse generator 30 is the "red on" signal and signal D is the "red sample" signal which is the trailing portion of the "red on" signal. The trailing portions of the "on" signals are used as the "sample" portions to allow the waveform to stabilize before sampling.

The green control circuit is generally designated with reference numeral 32 within the dashed lines and the red control circuit is generally designated with reference numeral 34 within the other dashed lines. The green control signal will first be discussed.

The "green on" signal from line A is fed to the base of a PNP transistor 36. LED 10 is connected in the emitter-collector circuit of transistor 36 and thus when the base of transistor 36 is low, transistor 36 will be conducting and LED 10 will be effectively shorted. On the other hand, when the "green on" signal is fed to the base of transistor T1, the current will flow through LED 10 turning on this green LED. The current will flow through NPN transistor 38 which has its emitter grounded through resistor 40.

The circuit functions automatically to establish a reference standard for the intensity of the green light from LED 10. As stated above, photodetector 22 detects the intensity of light that is emitted by LED 10. Detector 22 provides a current that is proportional to this light intensity. As illustrated in FIG. 2, detector 22 is coupled to the negative input of an amplifier 42 having a feedback resistance 44, so that the current is converted to a voltage at the output of amplifier 42.

Thus the voltage at the output of amplifier 42 is proportional to the light intensity of LED 10. If there is no light from LED 10, there will be a zero voltage at the output of amplifier 42 or if there is maximum light intensity there will be maximum voltage at the output of amplifier 42.

The output of amplifier 42 is coupled via line 46 to an input electrode 48 of FET 50. The output electrode 52 of FET 40 is coupled to the negative input of reference amplifier 54 through a resistor 56. Amplifier 54, resistor 56 and a capacitor 58 serve as an integrator and the output of the integrator is fed via line 60 to the base of NPN transistor 38.

The frequency of the timing pulses may be 1 kilohertz although there is no limitation with respect thereto, other than as required by the amplifiers and photocells. If a frequency of 1 kilohertz is selected, every millisecond FET 48 will operate as a closed switch and the output of amplifier 42 is sampled by the integrator 54, 56, 58. If the output of amplifier 42 is zero, the input to the negative input of amplifier 54 will be zero which is lower than the reference input of amplifier 54. Thus, the output of amplifier 54 will be a positive voltage, biasing the base of NPN transistor 38 more positively and causing it to carry more current thereby increasing the intensity of LED 10. Each millisecond FET 50 will effectively operate as a closed switch and the sampling of the output of amplifier 42 will continue until the intensity of LED 10 reaches the unity reference which is set with respect to the integrator.

The integrator 54, 56, 58 is used to smooth out the sampling. It can be seen that FET 50 is only acting as a closed switch approximately one-quarter of the cycle (see FIG. 3) and the integrator acts to smooth out the current flow through the system.

Now referring to red control circuit 34 in FIG. 2, the "red on" signal C is fed via line 64 to the base of PNP transistor 66. When the base of transistor 66 is high, the transistor will be non-conducting and the current will flow through red LED 12 which is connected in the emitter-collector circuit of transistor 66. The current flow through LED 12 is controlled by the bias on the base of NPN transistor 68. The bias on the base of transistor 68 is responsive to the intensity of the light received at photodetector 24. The output of photodetector 24 is connected through a capacitor 70 to a preamplifier 72, the output of which is connected to electrode 76 of FET 76. The other electrode 78 of FET 76 is connected to the negative input of amplifier 80 through resistor 82. Amplifier 80, like amplifier 54, operates as an integrator with resistor 82 and capacitor 84.

At the output of amplifier 72 there is a resistor 86 and a capacitor 88 coupled to ground. Between resistor 86 and capacitor 88 a line 90 is coupled to the positive input of amplifier 80. Thus the positive input of amplifier 80 is continuously sampling the average signal at the output of amplifier 72. This is the average of the green and the red signal.

The circuit acts to compare the red signal with the average of the green and red signals. To this end, FET 76 is operated so that it acts as a closed switch only to pass the red signal to the negative input of the integrator 80. If the red signal is less than the average reference at the positive input of integrator 80, there will be a positive signal at the output of amplifier 80 which will render transistor 68 more conductive and thus more current will flow through LED 12 thereby increasing the intensity of the red signal. As the red signal increases, the average will also increase but since the green signal is not increasing at that time, the red signal will increase greater than the average signal will increase. Eventually the increase of the red signal will catch up to the average so that the average signal that is sensed at the output of amplifier 72 will be equal to the red signal that is sensed at the negative input of amplifier 80. When this occurs, the red intensity detected by photodetector 24 is equal to the green intensity detected by photodetector 24. Since the green LED and red LED are on alternately, photodetector 24 will first receive red light of a particular intensity, then green light of that identical intensity, then the red light of that particular intensity, then the green light of that same intensity, etc.

It can be seen that the circuit is operating so that photodetector 24 eventually receives the identical intensity of both the green light and the red light through the sample. A FET 92 is operated simultaneously with FET 76 so that the red light received by photodetector 22 is sampled by buffer amplifier 94. The RC circuit formed of resistor 96 and capacitor 98 acts to store the average red value at photodetector 22 and this value is fed to buffer amplifier 94 and the output across potentiometer 100 is equal to the ratio of the red absorbance to the green absorbance. Thus FET 92 acts as an open switch until line 102 carries the red signal.

In effect, the green intensity has been set by green control circuit 32 and the red intensity through the sample has been varied to match the green intensity through the sample by the control circuit 34. Once the red control circuit 34 provides LED 12 with the proper intensity (so that it matches the green intensity), the red intensity as detected by photodetector 22 is fed via line 102 to the sample and hold circuit to be averaged.

A shutoff control circuit 104 is coupled to potentiometer 100 and is operable to terminate predetermined functions if the red/green absorbance is above a preset level. Thus if hemoglobin is present in plasma 20 in excess of a predetermined value, shutoff control circiuit 104 will sense a high red/green absorbance level and will be operable to terminate the collection of the plasma.

Since both the red and green lights travel identical paths through the plasma 20, local disturbances such as air bubbles, fingerprints, scratches, etc. will affect both absorbances equally and will be of substantially no consequence. Also of little consequence will be the manner in which the sample holder is installed. Since the absolute quantity of ratio of color absorbances is the measured quantity instead of absolute level of attenuation, the apparatus does not require an operator zeroing procedure. The modulated nature of the LED's outputs cancels the problem of ambient light background. Of course, turbidity can be a chromatically selective phenomena depending upon the size of the particles. However, this ratio approach as described herein alleviates much of the error induced due to turbidity.

Although an illustrative embodiment of the invention has been shown and described, it is to be understood that various modifications and substitutions may be made without departing from the novel spirit and scope of the present invention.

What is claimed is:

1. A photometric apparatus for determining the absorbance ratio in a sample of two different wavelength lights, said apparatus comprising
    means for providing a light of a first wavelength having, when said first light is energized, a constant reference presample intensity before said first light is directed through the sample and a postsample intensity after said first light is directed through the sample;
    means for providing a light of a second wavelength having, when said second light is energized, presample and postsample intensities, respectively, before and after said second light is directed through the sample;
    means for alternately energizing said first and second lights;
    means for directing said alternately energized first and second lights through the sample;
    means for detecting said postsample intensity of said first and second lights;
    means for varying said postsample intensity of said second light until said postsample intensity of said second light is equal to said postsample intensity of said first light;
    means operative, after said postsample intensity of said second light equals said postsample intensity of said first light, for detecting the then prevailing presample intensity of said second light;
    whereby the then prevailing presample intensity of said second light is equivalent to the ratio of the absorbance in the sample of said second light and said first light.

2. An apparatus according to claim 1
    and further including means for averaging said postsample intensities of said first and second lights, and
    wherein said postsample intensity varying means is operative for equalizing said postsample intensity of said second light with said average until said postsample intensity of said second light equals said postsample intensity of said first light.

3. A photometric apparatus for detecting the absorbance ratio in a sample of two lights having different wavelengths, said apparatus comprising
    means for providing a first light of a first wavelength having, when energized, presample and postsample intensities, respectively, before and after said first light is directed through the sample;
    means for providing a second light of a second wavelength having, when energized, presample and postsample intensities, respectively, before and after said second light is directed through the sample;
    means for alternately energizing said first and second lights;
    means for detecting said presample intensity of said first light;
    means for varying said presample intensity of said first light until it is equal to a predetermined constant reference intensity;

means for directing said alternately energized first and second lights through the sample;

means for detecting said postsample intensity of said first and second lights;

means for varying said postsample intensity of said second light until said postsample intensity of said second light is equal to said postsample intensity of said first light;

means operative, after said postsample intensity of said second light equals said postsample intensity of said first light, for detecting the then prevailing intensity of said second light, whereby the then prevailing presample intensity of said second light is equivalent to the ratio of the absorbance in the sample of said second light and said first light.

4. An apparatus according to claim 3 and further including means for averaging said postsample intensities of said first and second lights, and wherein said postsample intensity varying means is operative for equalizing said postsample intensity of said second light with said average until said postsample intensity of said second light equals said postsample intensity of said first light.

5. A photometric apparatus for directing in a sample the ratio of the absorbance of two lights having differing wavelengths, said apparatus comprising:

means for providing a first light of a first wavelength and for providing a light of a second wavelength each of said first and second lights having, when energized, presample and postsample intensities, respectively, before and after said respective light is directed through the sample, means for alternately energizing said first and second lights;

a beam splitter positioned adjacent said first and second lights, with each of said first and second lights being directly substantially perpendicularly with respect to each other;

first photodetector means positioned on the opposite side of said beam splitter from said second light and operative for detecting said presample intensities of said first and second lights, second photodetector means positioned on the opposite side of said beam splitter from said first light and operative for detecting said postsample intensities of said first and second lights;

a sample holder located between said second detector means and said beam splitter;

means coupled to said first photodetector means and to said first light means for varying said presample intensity of said first light until it is equal to a constant predetermined reference intensity;

means coupled to said second photodetector means and to said second light means for varying said postsample intensity of said second light until it equals said postsample intensity of said first light; and means coupled to said first photodetector means operative, after said postsample intensity of said second light equals said postsample intensity of said first light, for detecting the then prevailing presample intensity of said second light, whereby the then prevailing presample intensity of said second light is equivalent to the ratio of the absorbance in the sample of said second light and said first light.

6. An apparatus according to claim 5 and further including means for averaging said postsample intensities of said first and second lights, and wherein said means for varying said postsample intensity of said second light is operative for equalizing said postsample intensity of said second light with said average until said postsample intensity of said second light equals said postsample intensity of said first light.

7. A method for determining the absorbance in a sample of two lights having different wavelengths, which comprises the steps of:

energizing a first light of a first wavelength having a constant reference intensity before it is passed through a sample;

alternately energizing a second light of a second wavelength;

directing the first light and the second light through a sample and detecting the intensity of the first and second lights after they have passed through the sample;

varying the intensity of the second light that has passed through the sample so that it is equal to the intensity of the first light that has passed through the sample; and detecting, after the intensity of the second light that has passed through the sample is equal to the intensity of the first light that has passed through the sample, the then prevailing intensity of the second light in a state wherein it has not passed through the sample, whereby the then prevailing intensity of the second light that has not passed through the sample is equivalent to the ratio of the absorbance of the second light and the first light.

8. A method according to claim 7 and further including the step of averaging the intensities of the first light and the second light that have passed through the sample, and wherein said step of varying the intensity of the second light includes utilizing this average as a reference for the control of the intensity of the second light passing through the sample until equalization between the first and second lights occurs.

9. A method of determining the absorbance in a sample of two lights having different wavelengths, which comprises the steps of:

energizing a first light of a first wavelength;

alternately energizing a second light of a second wavelength;

detecting the intensity of said first light;

varying the intensity of said first light so that it is equal to a predetermined reference intensity;

directing the first light and the second light through a sample and detecting the intensity of the first and second lights after they have passed through the sample;

varying the intensity of the second light that has passed through the sample so that it is equal to the intensity of the first light that has passed through the sample; and detecting, after the intensity of the second light that has passed through the sample is equal to the intensity of the first light that has passed through the sample, the then prevailing intensity of the second light in a state wherein it has not passed through the sample, whereby the then prevailing intensity of the second light that has not passed through the sample is equivalent to the ratio of the absorbance of the second light and the first light.

10. An apparatus for detecting the presence of hemoglobin in a fluid, which comprises:
   means for providing a substantially green light having, when said green light is energized, a constant reference presample intensity before said green light is directed through the fluid and a postsample intensity after said green light is directed through the fluid.
   means for providing a substantially red light having, when energized, presample and postsample intensities, respectively, before and after said red light is directed through the fluid;
   means for alternately energizing said green and red lights;
   means for directing said alternately energized green and red lights through the fluid;
   means for detecting said postsample intensity of said green and red lights;
   means for varying said postsample intensity of said red light until said postsample intensity of said red light is equal to said postsample intensity of said green light; and
   means operative, after said postsample intensity of said red light is equal to said postsample intensity of said green lights, for detecting the then prevailing presample intensity of said red light in a state in which it has not passed through the fluid, whereby the then prevailing presample intensity of said red light is equivalent to the ratio of the absorbance in the fluid of said red light and said green light.

11. An apparatus according to claim 10 and further including means for averaging said postsample intensities of said green and red lights, and wherein said postsample intensity varying means is operative for equalizing said postsample intensity of said red light with said average until said postsample intensity of said red light equals said postsample intensity of said green light.

12. An apparatus according to claim 1 or 3 or 5 or 10 and further including means responsive to the ratio of the absorbance of said lights for operating a predetermined function.

13. A method for detecting hemoglobin in a fluid, which comprises the steps of:
   energizing a substantially green light having a constant reference intensity before it is passed through the fluid;
   alternately energizing a substantially red light;
   directing the green light and the red light through the fluid and detecting the intensity of the green and red lights after they have passed through the fluid;
   varying the intensity of the red light that has passed through the fluid so that it is equal to the intensity of the green light that has passed through the fluid; and
   detecting, after the intensity of the red light that has passed through the fluid is equal to the intensity of the green light that has passed through the fluid, the then prevailing intensity of the red light in a state wherein it has not passed through the fluid, whereby the then prevailing intensity of the red light that has not passed through the fluid is equivalent to the ratio of the absorbance of the red light and the green light.

14. A method according to claim 13 and further including the step of averaging the intensities of the green light and the red light that have passed through the fluid, and wherein said step of varying the intensity of the red light utilizes this average as a reference for the control of the intensity of the red light passing through the fluid until equalization between the red and green lights occurs.

15. A method for detecting the presence of hemoglobin in a fluid utilizing a ratio of absorbance of two lights having different wavelengths, which method comprises the steps of:
   energizing a substantially green light;
   alternately energizing a substantially red light;
   detecting the intensity of said green light;
   varying the intensity of said green light so that it is equal to a predetermined reference intensity;
   directing the green light and the red light through the fluid and detecting the intensity of the green and red lights after they have passed through the fluid;
   varying the intensity of the red light that has passed through the fluid so that it is equal to the intensity of the green light that has passed through the fluid; and
   detecting, after the intensity of the red light that has passed through the fluid is equal to the intensity of the green light that has passed through the fluid, the then prevailing intensity of the red light in a state wherein it has not passed through the fluid, whereby the intensity of the red light that has not passed through the fluid is equivalent to the ratio of the absorbance of the red light and the green light.

16. A method according to claim 15 and further including the step of averaging the intensities of the green light and red light that have passed through the fluid, and wherein said step of varying the intensity of the red light utilizes this average as a reference for the control of the intensity of the red light passing through the fluid.

17. A method according to claim 7 or 9 or 13 or 15 and further including a step of operating a predetermined function in response to the ratio of the absorbance of the lights.

* * * * *